United States Patent
McConnell

(12) 
(10) Patent No.: US 6,283,938 B1
(45) Date of Patent: Sep. 4, 2001

(54) MEDICATING BANDAGE AND CONTROLLABLE PERMEABLE MEMBRANE

(76) Inventor: Daniel E. McConnell, 2115 St. Mary's St., Raleigh, NC (US) 27608

( * ) Notice: Subject to any disclaimer, the term of this patent is extended or adjusted under 35 U.S.C. 154(b) by 0 days.

(21) Appl. No.: 09/304,873

(22) Filed: May 4, 1999

(51) Int. Cl.[7] ................................................. A61M 31/00
(52) U.S. Cl. ............................................................. 604/66
(58) Field of Search ..................... 604/65–67, 361, 604/318; 600/300; 602/41, 42, 43, 44, 45, 46, 47, 48, 49; 128/DIG. 12, 13

(56) References Cited

U.S. PATENT DOCUMENTS

| | | |
|---|---|---|
| 4,322,232 | 3/1982 | Beane . |
| 5,697,896 * | 12/1997 | McNichols et al. ................... 604/20 |
| 5,730,721 | 3/1998 | Hyatt et al. . |
| 5,879,292 | 3/1999 | Steinberg et al. . |
| 6,030,827 * | 2/2000 | Davis et al. ...................... 435/287.1 |

* cited by examiner

Primary Examiner—Manuel Mendez

(57) ABSTRACT

A medicating bandage in which a controllable permeable membrane is interposed between a medication contained in a bandage pad and the skin of a patient undergoing medication. Passage of the medication through the membrane and into contact with the patient is metered by controlling the permeability of the membrane, preferably under the control of a biosensor and a microcontroller. The combination of a sensor and a controllable permeable membrane has usefulness apart from the bandage pad and medication.

37 Claims, 3 Drawing Sheets

MEDICATING BANDAGE AND CONTROLLABLE PERMEABLE MEMBRANE

BACKGROUND OF THE INVENTION

This invention relates to a medicating bandage in which the application of a medication is controlled by a controllable permeable membrane in response to a sensed biological condition of a patient being medicated.

It has been proposed heretofore to supply medication to a patient through the use of a medicating bandage, in which a supply of a medication is contained within a pad forming a part of a bandage and is released to the surface of the pad and to the skin of a patient to whom or to which the bandage is applied. This technology has been implemented, for example, in connection with medications intended for pain and nausea relief as well as for some more controlled medications used in treatment of other conditions.

Bandage dosage technology, as developed up until the time of this invention, has relied upon delivery of the medication under the control essentially of only physical parameters set at the time of manufacture of the medicating bandage. By determining the physical characteristics of the bandage, a designer may select dosage levels and durations. While this limited level of dosage control has enabled commercially acceptable products, it is recognized that such medicating bandages have been incapable of adapting dosage processes to what may be changing patient conditions.

It has also been proposed heretofore to render a bandage "intelligent" to the limited extent of providing, in the bandage itself, a sensor which is capable of registering certain events and signaling occurrences of those events.

SUMMARY OF THE INVENTION

In accordance with the invention described more fully hereinafter, a medicating bandage which has a limited level of intelligence through the inclusion of a sensor is provided with extended capabilities so as to enable metered release of medication. This purpose is achieved by providing a controllable permeable member which is interposed between the medication contained in a bandage pad and the surface of the pad which contacts the skin of a patient being medicated. The controllable permeable member is connected with and responsive to the sensor, so that the release of medication from the bandage is metered in response to conditions sensed from the body of the patient undergoing medication.

In particular, it is contemplated that the sensor and the controllable permeable membrane be electrically operable, and that they be joined through a control circuit contained within the bandage pad which governs the release of medication in accordance with a sensed biological condition of the patient.

The combination of a sensor and a controllable permeable membrane are deemed to have usefulness outside of the medicating application.

BRIEF DESCRIPTION OF THE DRAWINGS

Some of the purposes of the invention having been stated, others will appear as the description proceeds, when taken in connection with the accompanying drawings, in which.

DESCRIPTION OF THE PREFERRED EMBODIMENT(S)

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of the invention. Accordingly, the description which follows is to be understood as being a broad, teaching disclosure directed to persons of skill in the appropriate arts, and not as limiting upon the present invention.

Figure 1:
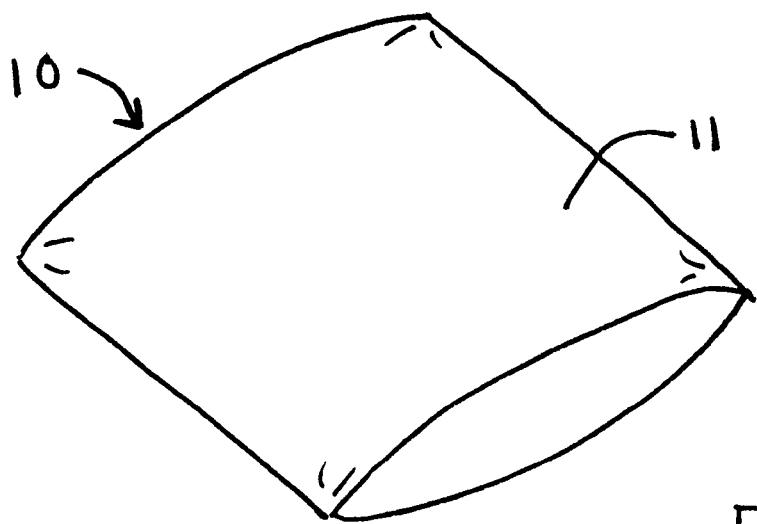
FIG. 1 is a perspective view of a bandage in accordance with this invention.

As illustrated in FIG. 1, the medicating bandage of this invention has a bandage pad 10 which is intended to be brought into contact with the skin of a patient undergoing medication. The pad 10 may be made of materials known in the manufacture of bandages, such as a textile fabric or web, fibrous mat, or the like. It is significant to the present invention that the pad have sufficient body and structural integrity to contain a number of elements of the present inventive combination within the pad. The pad 10 has a patient contacting surface 11.

Figure 2:
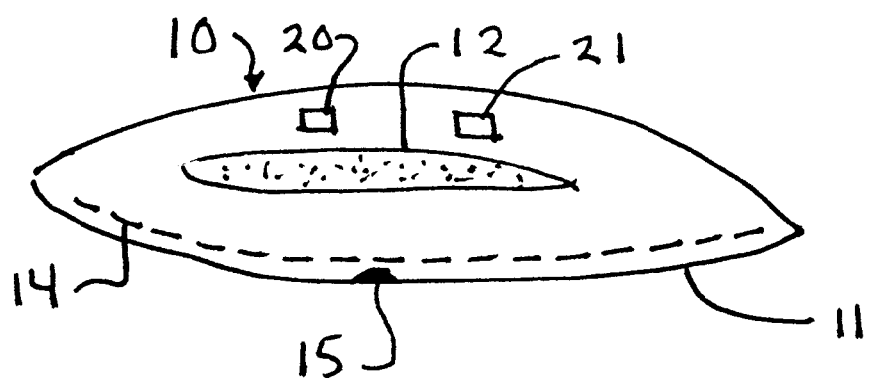
FIG. 2 is a sectional view through the bandage of FIG. 1; illustrating certain components of the bandage which are contained within a bandage pad.

Contained within the pad 10 is a medication, indicated at 12 in FIG. 2, to be supplied to the patient. The medication may take any form suitable for the application here described, such as being a paste, a suspension, a colloid, a solution or the like. Whatever form is chosen, it should be such that the medication is restrained against uncontrolled leakage or release in order that the controlled metering desired for this invention is accomplished. If necessary or appropriate, the medication can be contained within an appropriate wrapper or bag providing an impermeable membrane around portions of the medication which will be out of patient contact. It is contemplated, for certain applications of this invention as described more fully hereinafter, that the medication may have certain ionic characteristics, which may be imparted by a carrier material with which the medication is mixed to produce the solution, suspension, paste, etc.

Interposed between the medication 12 and the patient contacting surface 11 of the pad 10 is a permeable membrane 14 through which medication is metered to the patient. The membrane 14 is a controllable membrane, as brought out more fully hereinafter, in order that the medication be released to the patient in a metered, controlled manner. The medication 12 is a material whose passage through the membrane 14 is to be metered. The medication, which is located on what may be called a supply side of the membrane, is a material which can affect a condition on the patient contact, or delivery, side of the membrane. Passage of the medication through the membrane is metered in response to a sensor as described hereinafter so as to control that affect.

The controlled release of the medication is other than predetermined, however. This follows from certain significant characteristics of the medicating bandage of this invention arising out of the containment, in the pad 10, of a sensor 15 which, in a medicating application of the controllable permeable membrane, senses a biological characteristic of the patient undergoing medication. The sensor is a biosensor located to monitor conditions on the delivery side of the membrane.

The biosensor 15 is contemplated by this invention as a selected one of a variety of types, depending upon the biological characteristic to be sensed. For example, should the biological characteristic being sensed be skin temperature, then the sensor is selected to be some thermally responsive device such as a thermistor which is capable of being made of small physical dimensions and yet accurately reflect the temperature of surfaces with which it is brought into contact. Similarly, the sensor may be an electrical device (perhaps as simple as a pair of conductive members spaced one from another) which is responsive to surface electrical conductivity changes arising from the appearance of moisture such as sweat. By selection of a dielectric material separating such conductive members and/or a reagent permeating such a dielectric, such a sensor can be made to be responsive to surface chemistry, such as the appearance of certain characteristic chemicals in sweat or other bodily discharges such as blood. By spacing the conductive elements one from another with a material which is compressible, the sensor may be made responsive to contact pressure between the bandage pad and the patient. If an optical form of sensor is selected, then the sensor will be responsive to changes in coloration such as may result from infection of a wound, bruising, or the like. For some uses, it may be desirable to provide more than one type of sensor in a single bandage or to use one form of sensor in more than one way, thereby making the metering of medication responsive to at least two indicators of biological characteristics. For example, the compressible material which makes a sensor pressure responsive may also contain reagents which make the sensor chemically responsive or be absorptive so as to make the sensor responsive to surface electrical conductivity.

The biosensor 15, responding to the biological condition or conditions selected, generates a signal, preferably an electrical signal, indicative of a biological state of the patient. That signal controls the metering of the medication 12 through the membrane 14. Preferably, the membrane is an electrically controllable permeable membrane.

The present invention contemplates that a controllable permeable membrane may be formed in a number of ways, and further that at least certain of such membranes may cooperate in particular manners with characteristics of the medication. In particular, the membrane may cooperate with the medication to induce release or flow of medication, or may cooperate with the medication to impede or limit release or flow of medication. In the former instance, a medication formulation which has strong ionic characteristics may be induced to move through the membrane by the imposition of an electrical field drawing the medication toward the patient contact surface 11 of the pad 10. In the latter instance, the imposition of an electrical field may result in impeding or limiting such medication movement. By motivating or impeding medication movement, the medication is metered into contact with a patient and the medicating effect is controlled.

Figure 3:
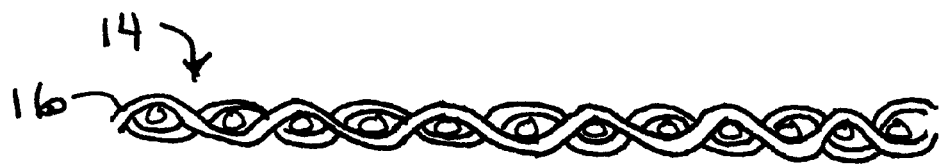
FIGS. 3, 4 and 5 are enlarged views of elements of a permeable membrane contained within the bandage pad.
Figure 4:
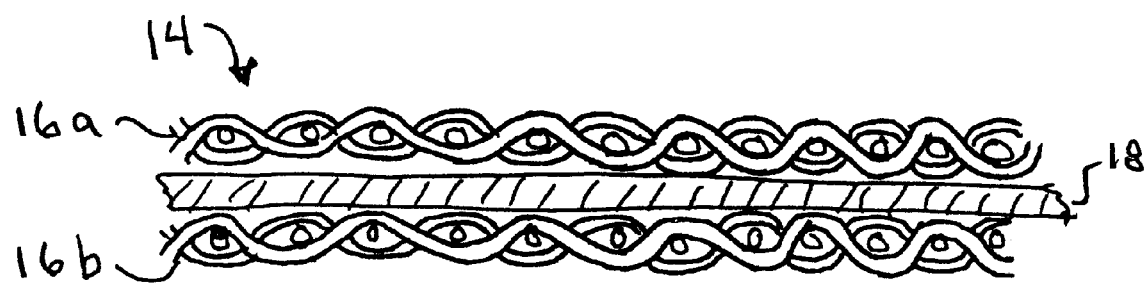
Figure 5:
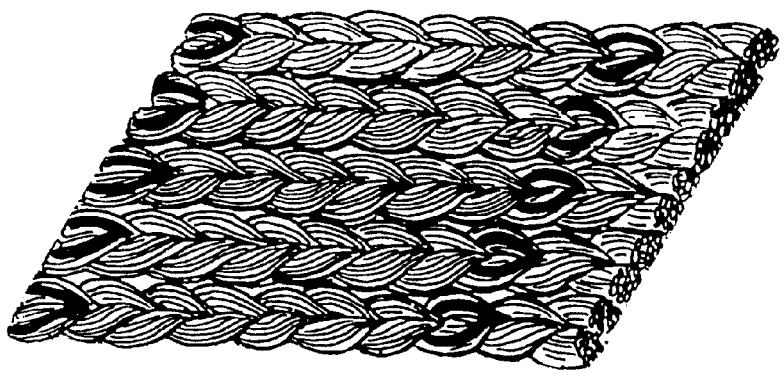

The present invention particularly contemplates that the controllable membrane be electrically controllable. In accordance with this invention, such a membrane has an electrically conductive web 16 (FIGS. 3, 4 and 5). The web 16 may be fabricated through using a number of techniques, including weaving (FIGS. 3 and 4) and knitting (FIG. 5). If woven, the web may use filaments or fibers which intersect at right angles, as a rectilinear weave, or at lesser included angles, as a triaxial weave. A triaxial weave may be preferable for certain critical medications, as such techniques result in a greater assurance of consistency in and more secure maintenance of the size of openings in the woven material. If knitted, the web may use filaments or fibers which are engaged one with another in a form of lock stitch, which also provides greater assurance of control of opening size than is the case with rectilinear weaving.

The web 16 will include at least a portion of electrically conductive filaments or fibers. Such filaments may, for example, by an extruded polymer containing a predetermined percentage of a conductive material such as carbon black, or may be a conductive material such as fine copper wire. The web 16 may be formed entirely of such conductive filaments or fibers, depending upon the precise nature of the medication to be controlled and the manner in which controlled metering is achieved. If a motivating field is to be used for control, then the web may have two electrically insulated circuits formed within the web, such as by selecting a weave or knit in which alternate fillings, warps, or courses have differing characteristics. For example, a rectilinear woven fabric useful as the web 16 may have alternate warp filaments which are dielectric material and conductive material, the dielectric warps serving to separate the conductive warps one from another. Thus the imposition of differing polarities of electromotive force on conductive warps which are insulated one from another will result in generation of an electrical field which may controllably motivate or impede medication movement toward the patient surface 11 of the pad 10 containing such a web 16.

An alternative to the structure just described can be the provision of a pair of conductive webs 16a and 16b (FIG. 4) which are spaced one from the other by a dielectric layer 18. The dielectric layer, in this instance, is available to serve additional purposes if desired, as described hereinabove with regard to the sensor 15. In such an instance, the sensor 15 and controllable membrane 14 have shared structure.

Yet another form for the conductive web 16 is derived from the use of an electrostrictive filament or fiber in the formation of the web. As here used, the reference to a filament or fiber as being electrostrictive refers to a characteristic of the filament or fiber of changing physical dimensions under the influence of an electrical current flow or field. Thus, if a filament or fiber formed of an electrostrictive material has an electrically conductive core, and an electrical current is passed therethrough, the effective diameter of the filament or fiber will change. Such changes can be used, in a woven or knit web, to controllable change the dimension of openings in the web and thereby control metering of medication through the membrane which includes the web.

Such an electrostrictive filament or fiber may also be used in the separating dielectric layer 18 interposed between two conductive webs, with a comparable result.

Figure 6:
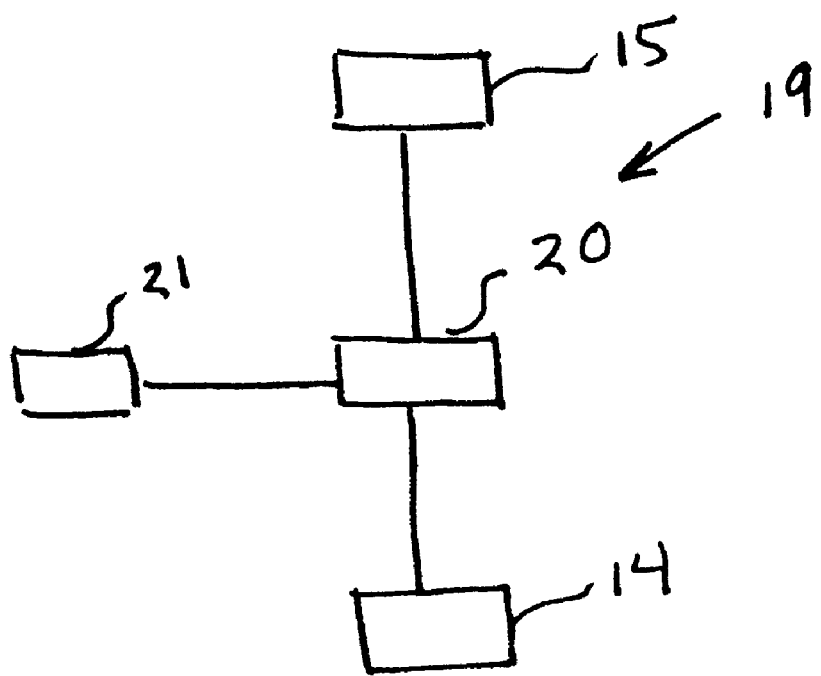
FIG. 6 is a schematic representation of the interconnection among elements of this invention which control the metered release of material.

In order to provide for an operative interconnection between the sensor 15 and the controllable membrane 14, the present invention preferably provides a control circuit 19 (FIG. 6). The control circuit 19 is connected with the sensor to receive therefrom a signal indicative of a biological state of a contacted body, and translates the received signal into a control signal which is then supplied to the membrane 14 to control metering of medication release. As will become clear, preferably the signals involved are electrical, and those signals must be at voltage and current levels and sufficiently isolated from bodily contact to avoid risk of injury to the patient.

The present invention contemplates that the control circuit 19 be composed of a microcontroller 20 and an associated memory device 21. The memory device is present to receive and store, preferably in digital form, instructions for the microcontroller regarding the manner in which the control circuit responds to the sensor signal in generating and applying the control signal. A digital program so stored is executable by the microcontroller to vary the control signal in predetermined manners relative to the sensor signal. For example, the microcontroller and memory device may cooperate to meter medication release as a linear function of the sensor signal between predetermined minima and maxima. That is, the stored program may predetermine minimal delivery rates for the medication and maximum delivery rates for the medication, and then vary the delivery rate between those minima and maxima in response to the sensor signal. The minima may be selected to be a zero delivery rate or some floor rate above zero. The maxima may be selected to exhaust the supply of medication as quickly as possible or at some slower rate.

The microcontroller 20, memory device 21 and stored program may be configured to meter medication release as a nonlinear function of the sensor signal. Alternatively, they may be configured to meter medication release as a linear or nonlinear function which takes into consideration the passage of time.

From the foregoing description of structure, it will be understood that in using the medicating bandage of this invention a method is followed which includes steps of applying a bandage pad containing a medication and a biosensor to the skin surface of a patient; sensing with the biosensor a biological state of the patient; and metering the release of medication to the skin surface of the patient under the control of a microcontroller contained in the pad. As will be understood from the discussion above, the metering preferably is done by controlling the passage of medication through a controllable permeable membrane interposed between the medication contained in the pad and the skin contacting surface of the pad. This is accomplished by generating at the biosensor an electrical signal indicative of the biological state of the patient, supplying the generated signal to the microcontroller, generating at the microcontroller a control signal which is a function of the electrical signal, and supplying the control signal to the controllable permeable membrane.

In the drawings and specifications there has been set forth a preferred embodiment of the invention and, although specific terms are used, the description thus given uses terminology in a generic and descriptive sense only and not for purposes of limitation. In particular, while disclosed for particular utility in the control of medication, it is believed that the electrically controllable permeable membrane of this invention and its cooperation with a sensor responsive to conditions on a delivery side of the membrane has wider utility.

What is claimed is:

1. A bandage comprising:
   a pad having a body contacting surface;
   a biosensor contained in said pad to provide a signal indicative of a biological state of a contacted body;
   a biologically active medication contained in said pad; and
   a controllable permeable membrane interposed between said medication and said body contacting surface and connected to said biosensor to respond to said signal by metering release of said medication at said body contacting surface.

2. A bandage according to claim 1 wherein said biosensor provides a signal indicative of at least one of (a) the temperature characteristics of a contacted body surface and (b) the surface electrical conductivity of a contacted body surface and (c) the surface chemistry characteristics of a contacted body surface and (d) the contact pressure exerted between said pad and a contacted body surface and (e) the coloration characteristics of a contacted body surface.

3. A bandage according to claim 1 wherein said biosensor provides a signal indicative of the temperature characteristics of a contacted body surface.

4. A bandage according to claim 1 wherein said biosensor provides a signal indicative of the surface electrical conductivity characteristics of a contacted body surface.

5. A bandage according to claim 1 wherein said biosensor provides a signal indicative of the surface chemistry characteristics of a contacted body surface.

6. A bandage according to claim 1 wherein said biosensor provides a signal indicative of the contact pressure characteristics between said pad and a contacted body surface.

7. A bandage according to claim 1 wherein said biosensor provides a signal indicative of the coloration characteristics of a contacted body surface.

8. A bandage according to claim 1 wherein said biosensor provides a signal indicative of at least two of the temperature, surface electrical conductivity, surface chemistry, and coloration characteristics of a contacted body surface.

9. A bandage comprising:
   a pad having a body contacting surface;
   a biosensor contained in said pad to provide an electrical signal indicative of a biological state of a contacted body;
   a biologically active medication contained in said pad;
   an electrically controllable permeable membrane interposed between said medication and said body contacting surface to meter release of said medication at said body contacting surface; and
   a control circuit contained in said pad and operatively interconnecting said biosensor and said membrane for translating said signal into a control signal provided to said membrane to control metering of medication release.

10. A bandage according to claim 9 wherein said control circuit comprises a microcontroller contained within said pad and a memory device connected to said microcontroller and storing a digital program executable by said microcontroller to vary said control signal in a predetermined manner in response to said signal.

11. A bandage according to claim 10 wherein said microcontroller and said memory device cooperate to meter medication release as a linear function of said signal between predetermined minima and maxima.

12. A bandage according to claim 10 wherein said microcontroller and said memory device cooperate to meter medication release as a nonlinear function of said signal between predetermined minima and maxima.

13. A bandage according to claim 10 wherein said microcontroller and said memory device cooperate to meter medication release as a function of said signal and of the passage of time.

14. A bandage according to claim 9 wherein said electrically controllable permeable membrane cooperates with said medication to induce flow of said medication to said contact surface.

15. A bandage according to claim 9 wherein said electrically controllable permeable membrane cooperates with said medication to limit flow of said medication to said contact surface.

16. A bandage according to claim 9 wherein said electrically controllable permeable membrane comprises an electrically conductive web.

17. A bandage according to claim 16 wherein said web comprises knitted together electrically conductive strands.

18. A bandage according to claim 16 wherein said web comprises woven together electrically conductive strands.

19. A bandage according to claim 16 wherein said electrically controllable permeable membrane comprises a pair of electrically conductive webs spaced one from the other by a dielectric layer.

20. A bandage according to claim 19 wherein each of said webs comprises knitted together electrically conductive strands.

21. A bandage according to claim 19 wherein each of said webs comprises woven together electrically conductive strands.

22. A bandage according to claim 16 wherein said electrically controllable permeable membrane comprises an electrostrictive web.

23. A bandage according to claim 22 wherein said web comprises knitted together electrically conductive strands.

24. A bandage according to claim 22 wherein said web comprises woven together electrically conductive strands.

25. A bandage comprising:
   a pad having a body contacting surface;
   a biosensor contained in said pad to provide an electrical signal indicative of a biological state of a contacted body;
   a biologically active medication contained in said pad;
   an electrically controllable permeable membrane having an electrically conductive web interposed between said medication and said body contacting surface to meter release of said medication at said body contacting surface; and
   a microcontroller and a memory device connected to form a control circuit contained in said pad and operatively interconnecting said biosensor and said web and translating said signal into a control signal provided to said membrane to control metering of medication release as a function of said signal.

26. A method comprising:
   applying a bandage pad containing a medication and a biosensor to the skin surface of a patient;
   sensing with the biosensor a biological state of the patient; and
   metering the release of medication to the skin surface of the patient under the control of a microcontroller contained in the pad by controlling the passage of medication through a controllable permeable membrane interposed between the medication contained in the pad and the skin contacting surface of the pad and operatively connected to the microcontroller.

27. A method according to claim 26 wherein the step of controlling the passage of medication comprises generating at the biosensor an electrical signal indicative of the biological state of the patient, supplying the generated signal to the microcontroller, generating at the microcontroller a control signal which is a function of the electrical signal, and supplying the control signal to the controllable permeable membrane.

28. Apparatus comprising:
   an electrically controllable permeable membrane which meters the passage of a material therethrough from a supply side to a delivery side and
   a sensor responsive to conditions on the delivery side of the membrane and which generates an electrical signal indicative of a condition which can be affected by the material;
   said sensor being connected to said membrane and said membrane being responsive to said signal for varying the metering of the material.

29. Apparatus according to claim 28 wherein said electrically controllable permeable membrane comprises an electrically conductive web.

30. Apparatus according to claim 29 wherein said web comprises knitted together electrically conductive strands.

31. Apparatus according to claim 29 wherein said web comprises woven together electrically conductive strands.

32. Apparatus according to claim 32 wherein said electrically controllable permeable membrane comprises a pair of electrically conductive webs spaced one from the other by a dielectric layer.

33. Apparatus according to claim 32 wherein each of said webs comprises knitted together electrically conductive strands.

34. Apparatus according to claim 32 wherein each of said webs comprises woven together electrically conductive strands.

35. Apparatus according to claim 29 wherein said electrically controllable permeable membrane comprises an electrostrictive web.

36. Apparatus according to claim 35 wherein said web comprises knitted together electrically conductive strands.

37. Apparatus according to claim 35 wherein said web comprises woven together electrically conductive strands.

* * * * *